United States Patent [19]

Nagy et al.

[11] Patent Number: 4,882,930
[45] Date of Patent: Nov. 28, 1989

[54] MELT INDEXER SYSTEM WITH ROBOT OPERATION

[75] Inventors: Gabor S. Nagy, Waxhaw, N.C.; Richard C. Akeson, Cedarberg, Wis.; Richard E. Sweenie, Watertown, Wis.; Mark E. Novak; Harry K. Malsch, both of Milwaukee, Wis.; Thomas J. Widule, Elm Grove, Wis.; Gustav L. P. Ding, Milwaukee, Wis.; Jared K. Jackson, Brookfield, Wis.

[73] Assignee: Automatik Machinery Corporation, Charlotte, N.C.

[21] Appl. No.: 208,742

[22] Filed: Jun. 17, 1988

[51] Int. Cl.$^4$ ............................................. G01N 11/04
[52] U.S. Cl. ......................................................... 73/56
[58] Field of Search ............................................ 73/56

[56] References Cited

U.S. PATENT DOCUMENTS

| | | | |
|---|---|---|---|
| 3,203,225 | 8/1965 | Sieglaff et al. | 73/56 X |
| 3,625,050 | 12/1971 | Noetzel et al. | 73/56 |
| 3,758,776 | 9/1973 | Frohne et al. | 73/56 X |
| 4,096,739 | 6/1978 | Barker et al. | 73/56 |

Primary Examiner—Stewart J. Levy
Assistant Examiner—Joseph W. Roskos
Attorney, Agent, or Firm—W. Thad Adams, III

[57] ABSTRACT

A melt indexer system for determining the melt index of a plastic by testing. The melt indexer system comprises a plurality of melt indexers, each of the melt indexers including a melt chamber into which a sample of plastic to be tested is placed, a heater for melting the sample to a predetermined temperature and a test piston for extruding the melted sample through a calibrated orifice of a removable die to determine the viscosity of the sample as a function of its temperature. A robot arm and a computer programmable to control the movement of the robot arm are provided. An infeed queue holds in predetermined order a plurality of containers containing samples to be tested and a bar code reader identifies each sample to be tested. A test computer associates a particular sample with a predetermined plan for testing the sample, records and processes the melt index test results. A vacuum sipper extracts a charge of the sample from the sample container and places it in the melt chamber. A cleaning tool cleans the test piston and melt chamber after the test is complete and prepares the apparatus for the next test.

28 Claims, 3 Drawing Sheets

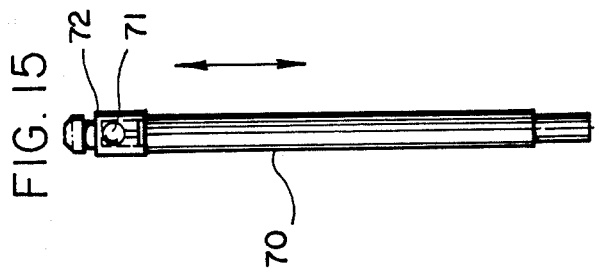
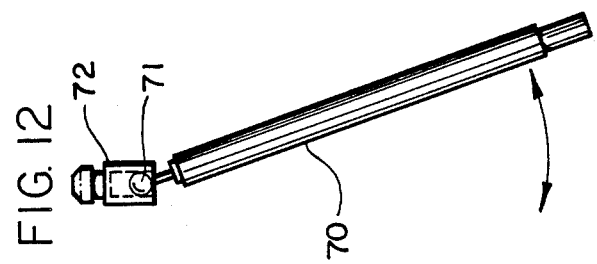
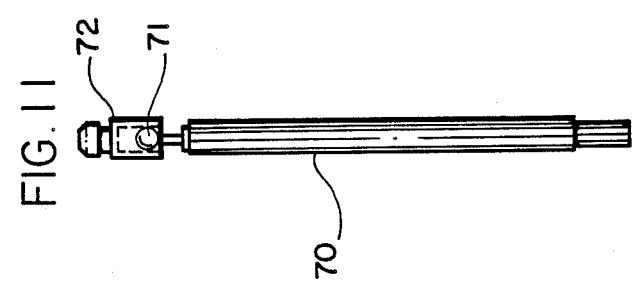

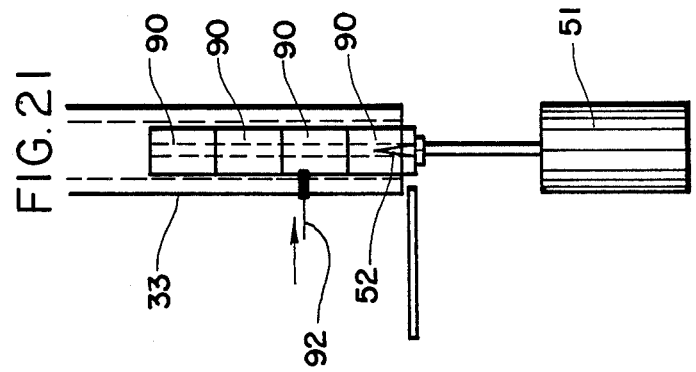
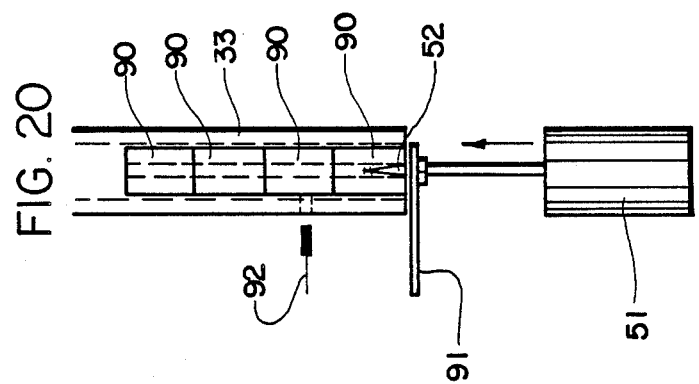
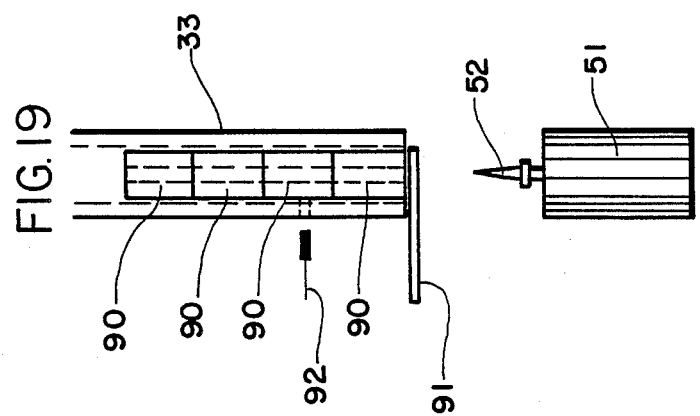

MELT INDEXER SYSTEM WITH ROBOT OPERATION

TECHNICAL FIELD AND BACKGROUND OF THE INVENTION

This invention relates to a melt indexer system wherein the steps required for carrying out the functions of the melt indexing tests are performed by a robot. In the embodiment disclosed in this application, three Goettfert Model MPE melt indexers, substantially modified for robot operation, are utilized. The Model MPE melt indexer is manufactured by Goettfert Werkstoff-Pruefmaschinen GmBH, Buchen/Odenwald, West Germany. A melt indexer is used to determine the relationship of the viscosity of a plastic material, such as a polymer, to its temperature. This information is necessary to control quality and consistency in polymer production essential to the proper uniformity and predictability of downstream characteristics of the polymer. These characteristics include, for example, elongation, reaction to dyestuffs, abrasion resistance to name only a few of many.

Presently, the MPE melt indexer is manipulated manually. Even though test consistency is essential, variations in operator technique substantially effect test results. In addition, the test presently requires close proximity between the operator and high heat. The work is tedious and not well suited to performance by human operators. However, due to the complexity of and the numerous variations in the test, manual operation of the melt indexer has heretofore been required.

In general, the melt indexer operates by heating to a precise temperature a carefully weighed sample of a plastic material in powder or granulated form. When heated, the plastic melts into a viscous mass. The heated mass of plastic is forced by a known weight through a die orifice of a known size. Sensors record data which permits a viscosity index to be determined from a relationship between the viscosity and the temperature of the molten plastic.

Characteristics inherent in the plastic material contribute significantly to the difficulty in achieving consistent test results from human operation of the indexer. The manner in which the indexer is cleaned between each test is particularly important, since any residue from a previous test not only contaminates the sample being tested, but interferes with the proper operation of the machine. Substantial variations in operator technique occur both between different operators and even the same operator from test-to-test and over time. Fatigue, work load and operator morale have all been identified as factors contributing to test inconsistency.

SUMMARY OF THE INVENTION

Therefore, it is an object of the invention to provide an automated test system for a melt indexer.

It is another object of the invention to provide a melt indexer which includes an automatic test system.

It is another object of the invention to provide a melt indexer and automatic test system which substantially reduces manpower requirements.

It is another object of the invention to provide a melt indexer and automatic test system which provides enhanced test results consistency.

It is another object of the invention to provide a melt indexer and automatic test system which provides automatic archiving test results.

These and other objects of the present invention are achieved in the preferred embodiments disclosed below by providing a melt indexer and an automated system for determining the melt index of a plastic by testing. The melt indexer has a melt chamber in which a sample of plastic to be tested is placed, heating means for melting the sample to a predetermined temperature and a test piston for extruding the melted sample through a calibrated orifice of a removable die to determine the viscosity of the sample as a function of its temperature. In combination with the melt indexer is an automated test system which comprises a robot arm and a computer programmable to control the movement of the robot arm. An infeed queue holds in predetermined order a plurality of containers containing samples to be tested. Identification means identify each sample to the tested and a test computer associates a particular sample with a predetermined plan for testing the sample, recording and processing the melt index test results.

Extracting means extract a charge of the sample from the sample container and place it in the melt chamber. Cleaning means clean the test piston and melt chamber after the test is complete and prepare the apparatus for the next test. Means for detecting and processing exceptions to proper operation of the apparatus are provided.

The robot arm is operable to take a container from the infeed queue, open the container, operate the extracting means to extract a charge from the sample container and place it in the melt chamber, and manipulate the cleaning means.

Preferably, the invention includes a plurality of melt indexers positioned in relation to each other and to the robot arm for being serviced, in turn, by the robot arm.

According to one preferred embodiment of the invention, a plurality of temperature queues are provided for holding a plurality of samples in a given order to be tested by a one of the plurality of melt indexers operating at the proper temperature for the sample.

Preferably, the identification means comprises a bar code reader for reading bar codes on the containers.

According to another preferred embodiment of the invention, the extracting means comprises a vacuum operated sipper for extracting a precise quantity of sample from the container and placing it in the melt chamber.

According to another preferred embodiment of the invention, the vacuum operated sipper extracts the sample to be tested from the container and places the sample in the melt chamber in increments, and wherein the melt indexer includes a tamping tool to move down the melt chamber between additions of the sample to the melt chamber to strip any sample on the sides of the melt chamber and compact the mass of melting sample at the bottom of the melt chamber. According to yet another preferred embodiment of the invention, the robot arm includes means for installing and removing the tamping tool and the test piston from the melt indexer.

Preferably, the cleaning means comprises means for brushing and/or ultrasonically treating the removed test piston, pressurizing means for pressurizing the test chamber with high pressure air to force out any sample remaining in the melt chamber after the melt indexing test is completed, means for removing the removable die from the bottom of the melt chamber for cleaning, and means for cleaning the melt chamber.

According to one preferred embodiment of the invention, the means for cleaning the melt chamber includes means for inserting a cloth cleaning patch over the melt chamber and forcing the patch down through the melt chamber to the bottom.

According to another preferred embodiment of the invention, means are provided for rotating the cloth patch as it is moved down the length of the melt chamber. According to yet another preferred embodiment of the invention, the cleaning means includes an ultrasonic bath for cleaning the removable die.

Preferably, the invention includes means for storing a plurality of removable dies for loading into the melt indexer by the robot arm.

According to one preferred embodiment of the invention, the container comprises a bottle with a screw cap, and means are provided for applying and removing caps from the bottle.

Preferably, the robot applies a predetermined low tightening torque for applying the cap to the bottle and a predetermined high torque for removing the cap from the bottle.

BRIEF DESCRIPTION OF THE DRAWINGS

Some of the objects of the invention have been set forth above. Other objects and advantages of the invention will appear as the description of the invention proceeds when taken in conjunction with the following drawings, in which:

FIGS. 11, 12 and 13 are views of the actions of the tamper;

FIGS. 19, 20, 21, 22 and 23 are sequential views of the operation of the die tool which performs die removal and retrieval from the die magazine;

DESCRIPTION OF THE PREFERRED EMBODIMENT

Glossary of Terms Used in Description

Figure 1:
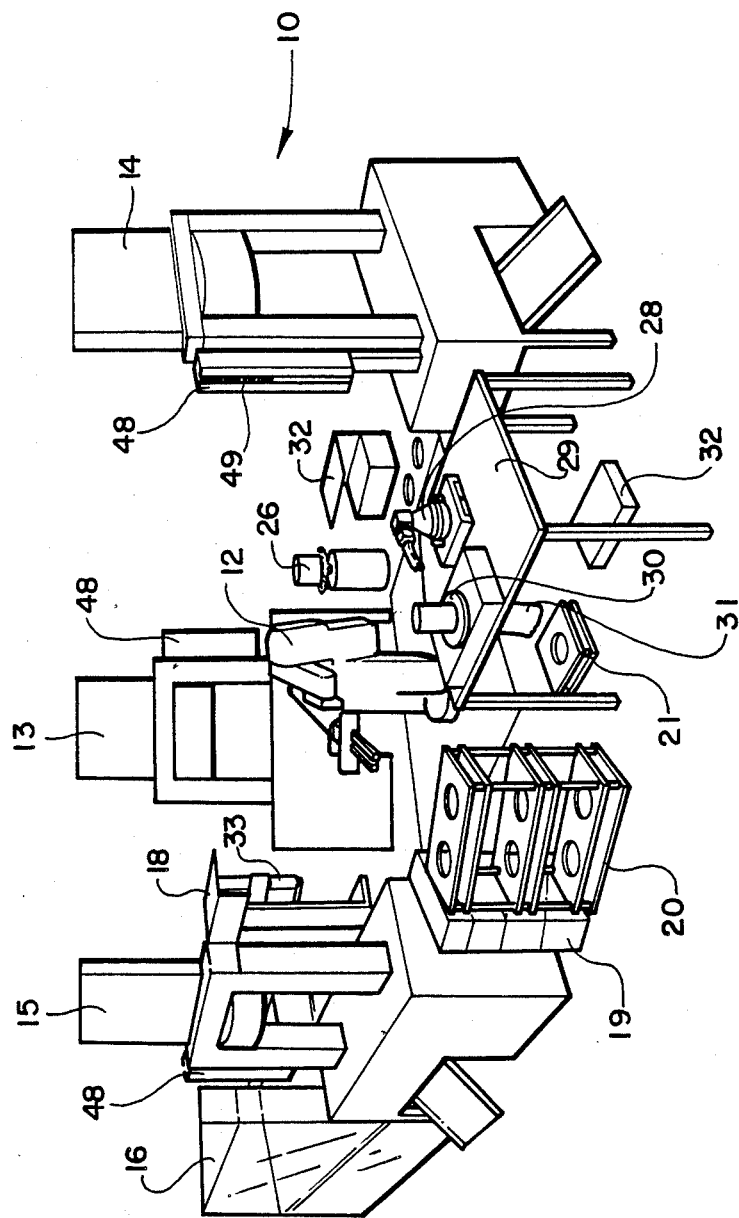
FIG. 1 is a overall system view of a prototype automated melt indexer.

Capper (31)—A mechanism for applying and removing the caps of bottles that are held in the robot's gripper. The capper is designed to apply gentle tightening torque and strong uncapping torque. A pulse width modulated signal is sent to the Robot Computer indicating the speed that the cap is turning. This signal is used to assure that the capper has a firm grip on the cap (by sensing no motion as the capper attempts to tighten the cap), and to indicate that the cap has been successfully removed (by sensing full speed rotation in the uncap direction). Capping Station—The place where the capper is located. Also at this location is a bar code reader, aligned to read bar codes on the bottle labels while the capper holds them by the cap and turns them. Cell (10)—The entire automated melt indexing system. Chamber Cleaning Tool (24)—A pneumatic tool having a long, rotating rod for the purpose of driving Cleaning Patches through the melt chamber in much the way one runs cleaning patches through a rifle bore. Chamber Pressurization Tool (75)—Fits into the tool holder of the MPE. When the MPE weights are lowered, the tool is pressed against the mouth of the melt chamber and can pressurize the chamber to force out Extrudate remaining in the die orifice and to force the die out of the chamber and onto the Die Tool. Class 1 Exception—A cell condition which requires immediate operator attention. e.g. The robot is unable to pull a patch from the Patch Dispenser, the remaining sample material is therefore about to harden in the melt chamber. Class 2 Exception—A cell condition which requires eventual operator attention. e.g. The patch supply is low, but not exhausted. Cleaning Patches (49)—Folded gauze pads used for cleaning the MPE melt chamber. Die—See Removable Die. Die Tool (51)—A vertical pneumatic cylinder with a pointed tip. Using this tool, the robot can reach up into the melt chamber of the MPE to insert and remove the Removable Dies. Die Magazine (33)—A vertical tube holding a large supply of clean Removable Dies, and provided with an escapement mechanism for loading a single die onto the tip of the Die Tool. Extrudate—The melted sample material that has been forced (extruded) through the Removable Die orifice. Infeed Queue (16)—The point where samples-to-be-tested enter the cell. A large serpentine path is used to allow the chute mechanism to contain up to about 50 sample bottles in a first-in-first-out queue which is filled at the top by the operator and emptied from the bottom by the robot. The bottom bottle in the infeed chute activates a sensor switch to let the cell computer know that a sample is available. Main Computer—This computer is the one that interfaces with the operator to create the Material Test Plans and Test Schedules. Bar code label printing is done by this computer. During operation of the cell, this computer assigns the Robot Computer different tasks and records the data from each test run. A WYSE model 2112 IBM-/AT compatible computer with an added IEEE 488 interface is used. The computer provides the operator interface for sample data input and test result output. The computer also provides operational control of the cell equipment. Material Test Plan—The "recipe" for how to test a particular material; including such things as the test temperature, the sample charge weight, the number of portions to divide the total charge into, and many other things. MPE (13, 14, 15)—A melt index testing machine, manufactured by Goettfert for manual operation and extensively modified for incorporation in the cell. Patch Dispenser (48)—A gravity feed mechanism that stores patches and makes them available to the robot grippers. The mechanism is fitted with two photo electric cells; the first to warn of a low patch supply, the second to verify that the robot has grasped a patch and pulled it out without having a second patch follow. Problem Output Chute (25)—This is the place that the cell deposits bottles that have no label, bottles with labels that don't make sense, bottles with caps that won't remove, and so on. Queue—Used as a noun, a queue is a waiting line, a first-in-first-out holding area or holding mechanism. Used as a verb, queue is the action of placing something into a FIFO holding mechanism. Removable Die (90)—A plug that is used at the bottom of the melt chamber in the MPE. The plug has a calibrated orifice in it through which the melted sample (extrudate) is forced by the pressure of overhead weights pressing down on the test piston. Robot Computer (12)—This computer controls the robot movements and MPE operations in response to high level commands from the main computer. An Intelledex Microsmooth 660 robot is used. The robot interfaces directly with the cell equipment for product flow through the system and for metering, charging, cleaning, and equipment movement. Digital I/O and serial interfacing in the proper quantities is provided. S1—The name given to a particular sample being processed through the cell in the "Narrative of Cell Operation." Sample Output Chute (24)—Samples are placed here when the cell is finished testing them. Tamper (70)—A specially constructed piston-like tool which fits into the tool holder of the MPE, and is used to compact the sample material in the melt chamber of the MPE. A ball joint at the top of the tamper allows it to remain in the tool holder and swing aside as the Vacuum Sipper deposits a sample portion into the melt chamber. Temperature Queues (19)—Physically, these are three Queues which hold samples waiting to be tested. The physical queue mechanisms are managed by the main computer to provide optimum system throughput. If two or more MPEs are operating at the same temperature, either of them can handle a particular sample that needs to be tested at that temperature. If the queues were each associated with an MPE, a sample might be placed in the queue for either machine, then be forced to wait as a very slow material ahead of it tied up the MPE. Samples arriving at the cell input later might be processed first because they happened to fall into a faster moving queue. The problem is resolved by treating the queues as queues of material to be processed at a certain temperature rather than queues of material destined for a particular MPE. The main computer merges two or more physical queues into one logical queue which serves all MPEs running at one temperature. Test Schedule—This is a schedule of what material is to be processed and at what times. The schedule is entered by the operator, typically at the beginning of the day, and at that time the associated bar code labels are printed. Vacuum Sipper (28)—A tool that the robot uses to withdraw sample material from the sample bottle and deposit it in the MPE melt chamber. Waste Chute—A silicone coated metal chute that conveys the waste extrudate from the area of the MPE to the Waste Bin.

DESCRIPTION OF BASIC SYSTEM PARTS

Figure 2:
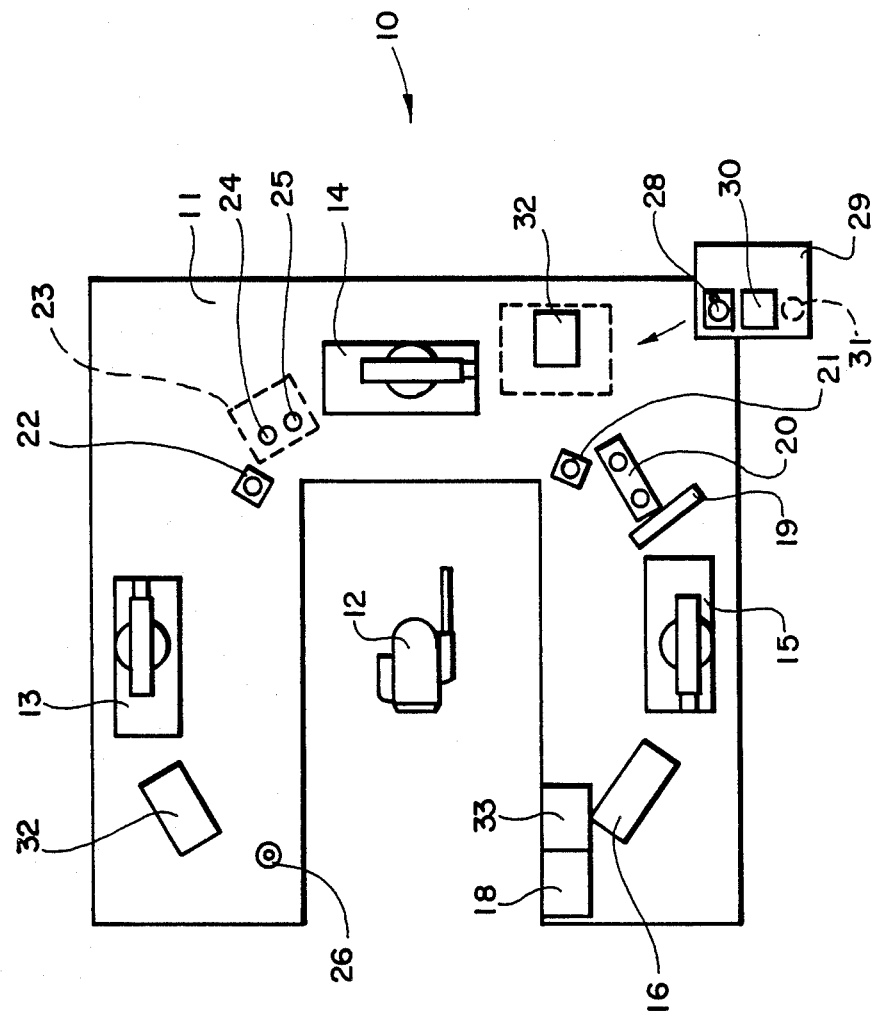
FIG. 2 is a schematic top plan view of a prototype automated melt indexer.

Referring now specifically to the drawings, an automated melt indexer system, or "cell", according to the present invention is shown in a prototype, perspective environmental view in FIG. 1 and a top plan view in FIG. 2. As is most clearly shown in FIG. 2, the melt indexer system 10 components, with the exception of the operating robot, are all positioned on a countertop 11 in spaced-apart relation to a floor surface on which robot 12 operates. As is best shown in FIG. 2, countertop 11 is substantially U-shaped to provide a generally circular configuration wherein most of the components are generally equidistant from the centrally placed robot 12. Access to the system components and to the robot 12 is had through the open end of countertop 11.

Three Goettfert MPE Melt indexers 13, 14 and 15 are positioned equidistantly around robot 12. Also positioned on countertop 11 are a sample infeed queue and priority infeed queue 16, a tool holder 18, a temperature queue 19, a standard queue 20, a pair of priority queues 21 and 22, and a disposal container 23 under the countertop 11 having a sample output chute 24 and a problem output chute 25 in countertop 11. A brush cleaner 26 cleans polymer from the various tools used in the melt indexer.

The melt indexer system 10 also includes a vacuum sipper 28 mounted on a raised table 29 sitting on countertop 11. A balance 30 is used to determine the amount of sample extracted from a bottle by the vacuum sipper 28. A capper 31 is positioned on the underside of table 29 in vertically spaced relation to the countertop 11. A bar code reader 32 is positioned on countertop 11 behind capper 31 and reads a bar code label of each bottle as its cap is removed.

An ultrasonic cleaner 32 is used to clean the various tools used by the robot 12. A die magazine 33 holds a plurality of dies 90 which are installed by the robot 12 in the respective melt indexers 13, 14 or 15, as needed.

Figure 3:
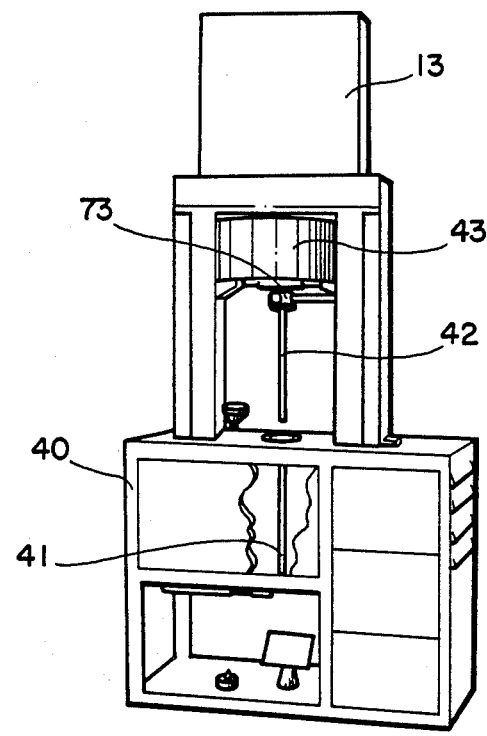
FIG. 3 is perspective view of a Goettfert melt indexer of the type used in the automated melt indexer according to the invention.

Referring now to FIG. 3, melt indexer 13 is shown. It is identical to melt indexers 14 and 15. It includes a cabinet 40 within which is contained sensors, heaters and other operating equipment, all of which function to determine the viscosity and hence the melt index of a plastic contained within a melt chamber 41. A test piston 42 mounted under weights 43 is lowered into the melt chamber 41 at the appropriate time and causes the molten polymer to be extruded through as orifice in a die 90 positioned in the bottom of melt chamber 41.

Figure 4:
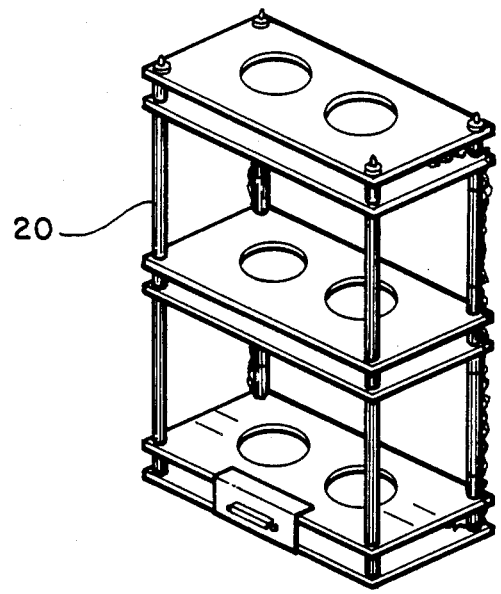
FIG. 4 is a perspective view of the standard queue.
Figure 5:
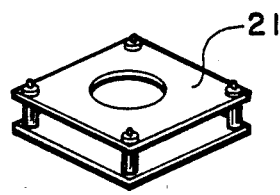
FIG. 5 is a perspective view of the priority queue.

As is shown in FIG. 4, the standard queue 20 holds a set of bottles containing polymers of known consistency and are used periodically to calibrate the melt indexers 13, 14 and 15. The priority queue 21 shown in FIG. 5 holds a sample contained in a bottle while awaiting availability of the melt indexer 13, 14 and 15 which is operating at the appropriate temperature for that sample.

Figure 6:
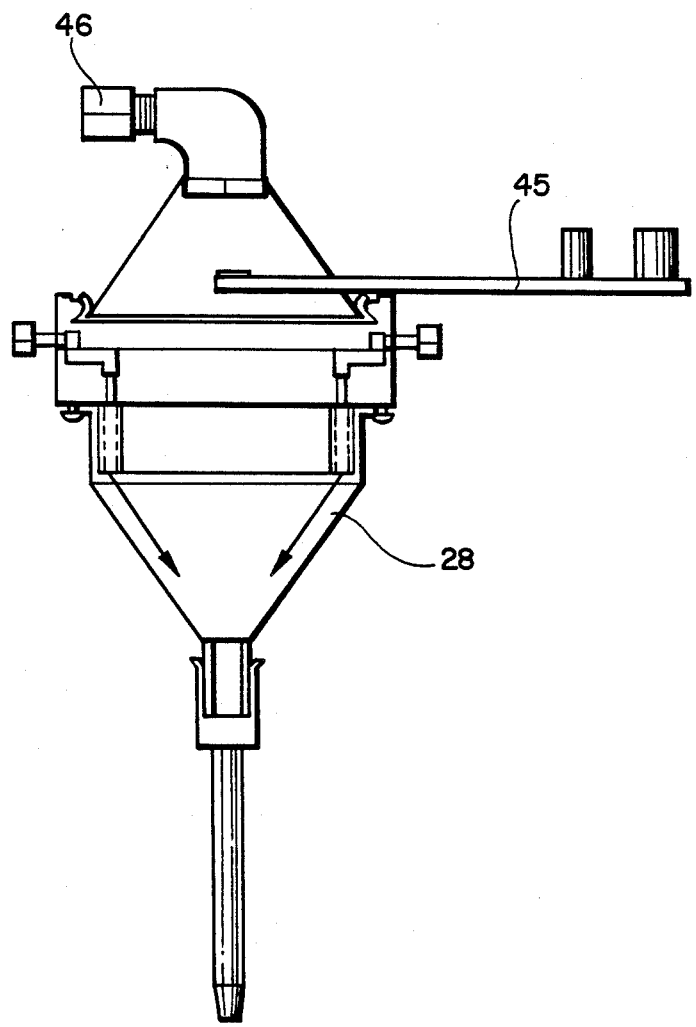
FIG. 6 is a side elevation of the vacuum sipper.
Figure 7:
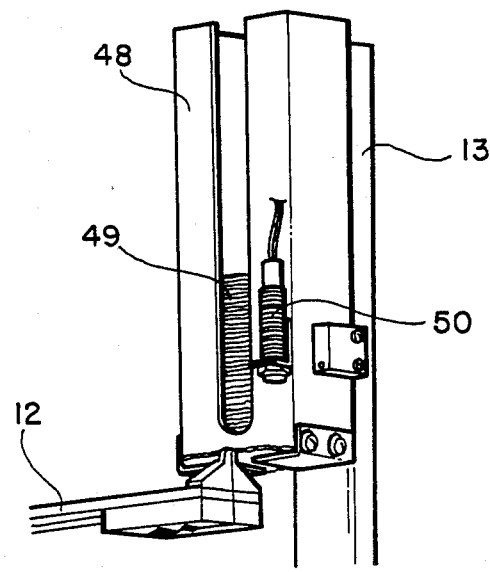
FIG. 7 is a perspective view of the patch dispenser.

The vacuum sipper 28 is shown in FIG. 6. The vacuum sipper 28 is grasped by the arm of the robot 12 by means of an outwardly extending finger 45. Vacuum is supplied to the vacuum sipper 28 from an vacuum source (not shown) through suitable feed lines (not shown) to a threaded collar 46.

A patch dispenser 48 is mounted on the side of each of the melt indexers 13, 14 and 15. Patch dispenser 48 contains a supply of gauze patches 49 which are used to clean the melt chamber 41 after each test. Patches are dispensed from the bottom of the patch dispenser 48, where the robot 12 grasps a patch and dispenses it from the bottom of the patch dispenser 48. A sensor 50 senses when the supply of patches 49 is low and alerts an operator to replenish the supply.

Figure 8:
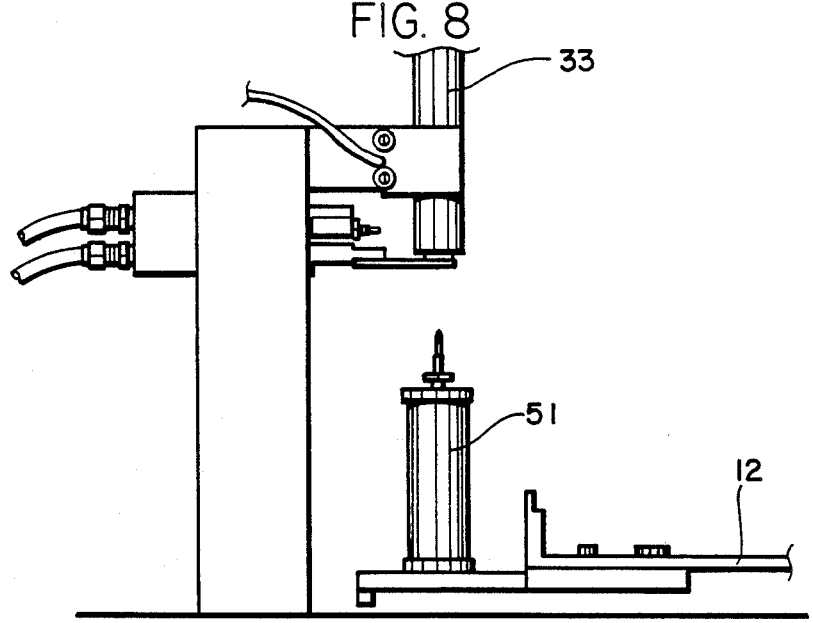
FIG. 8 is a side elevation view of the die tool and die magazine.

As is shown in FIG. 8, a die tool 51 is used to remove a die 90 from the die magazine 33. The die 90 is moved from the magazine to the bottom of melt chamber 41 and inserted into the bottom of the melt chamber 41. The function of the die tool 51 is explained in further detail with reference to FIGS. 20–24, below.

Figure 9:
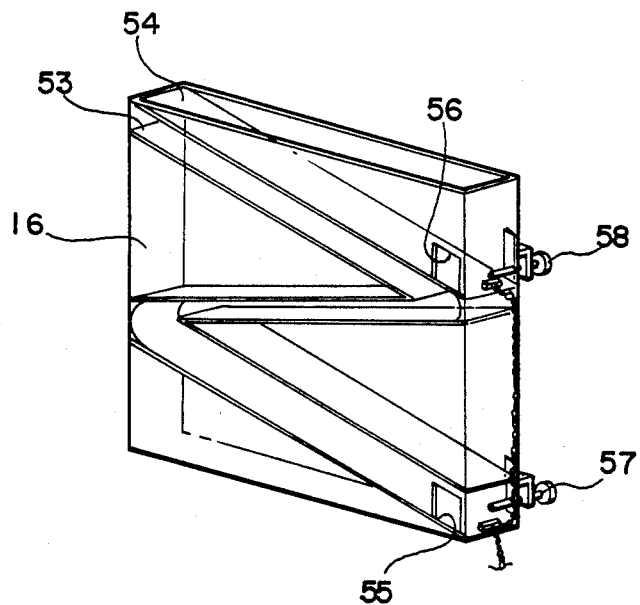
FIG. 9 is a perspective view of the priority and sample infeed queues.

FIG. 9 illustrates the sample infeed queue 16. Bottles may be introduced into the sample infeed queue through a regular entrance 53 or a priority entrance 54. Bottles are dispensed in a first-in, first-out (FIFO) manner. Therefore, if test is needed on a priority basis, the bottle is placed in the priority infeed queue which comprises the top surface of the entrance 53. Bottles are dispensed through a regular exit 55 and a priority exit 56 by spring loaded plungers 57 and 58, respectively. The plungers are operated by the robot 12.

Figure 10:
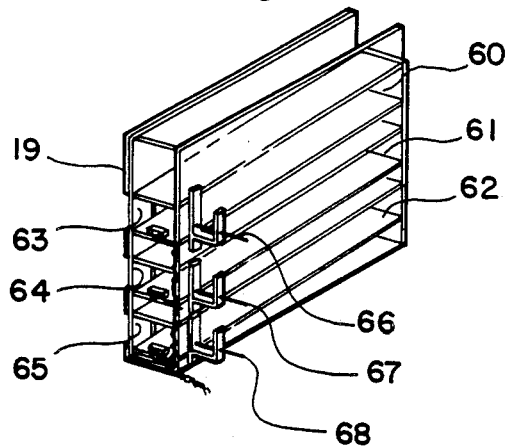
FIG. 10 is a perspective view of the temperature queue.

In FIG. 10, the temperature queue 19 is shown. If necessary, bottles removed from the sample infeed queue are placed in an appropriate chamber of the temperature queue 19 to await the appropriate melt indexer 13, 14 or 15 according to the temperature at which the sample is to be tested. The temperature queue 19 shown in FIG. 10 includes three inclined chambers 60, 61 and 62. Samples are removed through exits 63, 64 and 65 by spring loaded plungers 66, 67 and 68, respectively, by operation of the robot 12.

As is shown in FIGS. 11, 12 and 13, an articulated tamping tool 70 is suspended by a ball 71 retained in a ball socket 72 mounted in a chuck 73 on melt indexer 13. (See FIG. 3).

Figure 16:
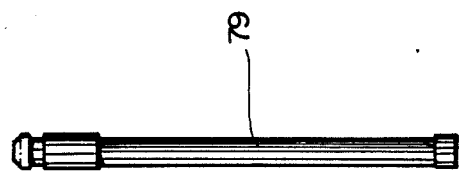
FIG. 16 is a side elevation of the melt chamber test piston.
Figure 15:
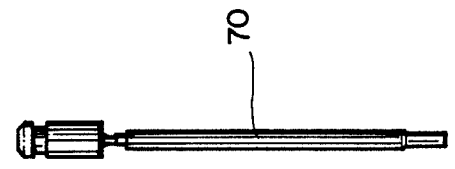
FIG. 15 is a side elevation of the tamper.
Figure 14:
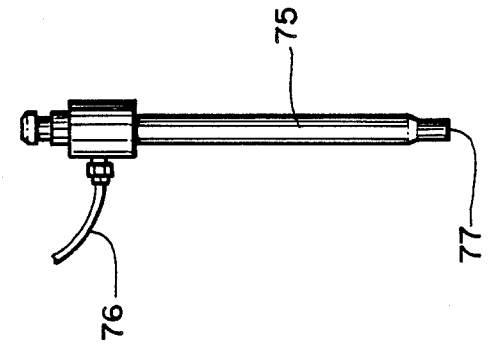
FIG. 14 is a side elevation view of the chamber pressurization tool.

FIG. 14 illustrates a chamber pressurization tool 75. Chamber pressurization tool receives compressed air from an air feed line 76 and expels compressed air through an outlet orifice 77 in its opposite end into melt chamber 41 to clean residual polymer from melt chamber 41 after each test. Tamper 70 (FIG. 15) and test piston 79 (FIG. 16) are successively placed in and removed from chuck 73 in melt indexer 13.

Figure 17:
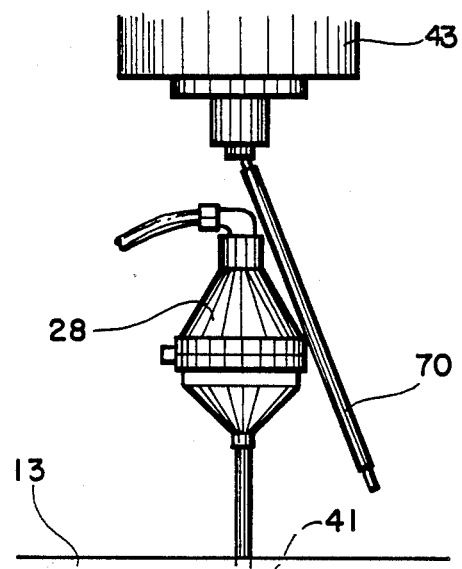
FIG. 17 is a side elevation view showing the sideways articulation of the tamper to allow access of the vacuum sipper to the melt chamber.

The articulation of tamping tool 70 is best shown in FIG. 17. The articulation is required in order to permit the vacuum sipper 28 to dispense polymer into melt chamber 41 after each tamping operation. The articulation of tamping tool 70 enables the charging and tamping operation to take place in relatively rapid alternating succession without the removal of the tamping tool 70.

Figure 18:
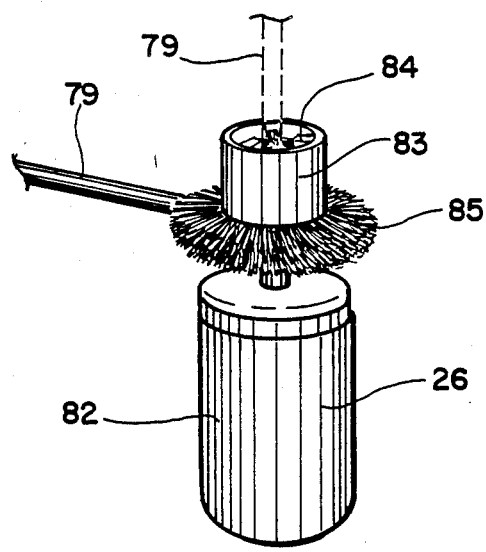
FIG. 18 is a perspective view of the tool cleaner brush.
Figure 24:
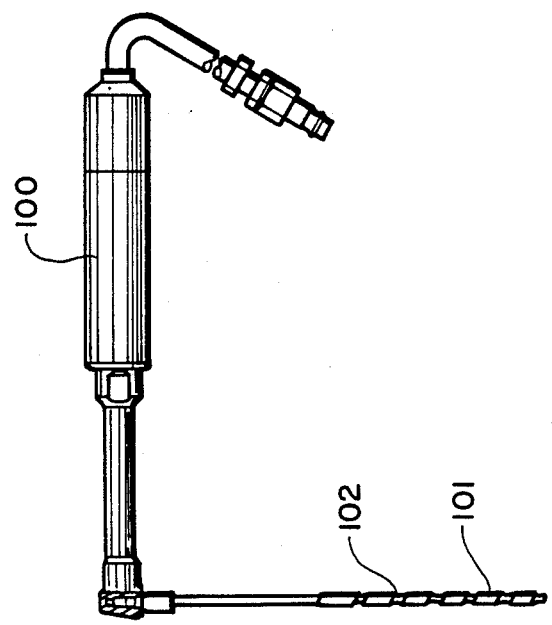
FIG. 24 is a side elevation view of the melt chamber cleaning tool.
Figure 23:
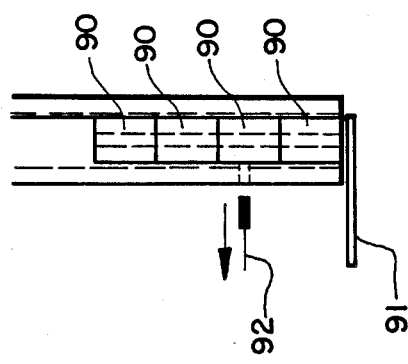

Brush cleaner 26 is shown in FIG. 18. The brush cleaner 26 comprises a motor 82 which rotates a housing 83 containing a series of interior brushes 84 and a set of exterior brushes 85. These brushes are used to clean the test piston 79 after each test operation. The sides of test piston 79 are cleaned by extending the test piston 79 down in between interior brushes 84. The end of test piston 79 is cleaned by placing the end of test piston 79 up against the outer edges of exterior brush 85. The test piston 79 is manipulated in the manner described above by robot 12. The operation of die tool 51 is illustrated in FIGS. 19–23.

Figure 22:
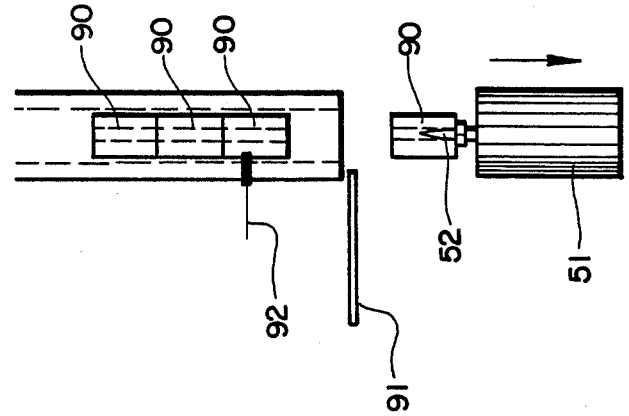

As is shown in FIG. 8, die tool 51 is contained on the end of an arm manipulated by robot 12. Robot 12 lifts the die tool 51, having an outwardly extending prong 52 thereon, into the bottom of die magazine 33. Die magazine 33 contains a plurality of stacked dies 90. Dies 90 are supported in die magazine by a movable die support 91 which extends over the bottom mouth of die magazine 33. Die support 91 has an elongate slot in one end which permits the prong 52 to be inserted into the lowermost die 90 (FIG. 20) with die support 91 thereafter being withdrawn. A lock 92 is extended through the side wall of die magazine 33 and prevents the second and successively stacked dies 90 from falling out when the lowermost die 90 is removed (FIG. 22). After the lowermost die 90 is removed, die support 91 is moved back into position and the lock 92 is then withdrawn in the manner shown in FIG. 23. Thereafter, die tool 51 moves the die to the bottom of melt chamber 41 for installation.

Melt chamber 41 is cleaned by a chamber cleaning tool 100 which comprises an air driven wrench having a reaming tool 101 mounted on one end thereof. A helical groove 102 may be provided and encourages a rotating, cleaning action by the gauze patch 49, as is described in further detail below.

System Setup

Material Test Plans

Prior to the testing of any specific compound by this system, the operator must have created a Material Test Plan detailing the test parameters for that compound. This task needs to be done only once per compound. Typical information in Material Test Plan will be:
Temperature at which the test is to be run;
Melt density;
Sample weight (a the nearest 0.5 gram);
Weight to apply during the test;
Weight to apply while tamping;
CORR value;
CODE value;
Number of portion splits (3 to 5);
SEL key to be used or not used (no multiple taps);
Print report (if allowed by Cell Configuration);
Standard or sample material
Number of cleaning patch passes;
Evaluate results, or log them;
  (max and min acceptable values)
  (alarm level, 0=log only
    1=log and activate user digital
    output contact
    ...
    9=log and declare Class 2);
Data collection to begin immediately or in the ASTM range; and
Number of sample points to take.
In order to minimize the opportunities for operator error, only one Material Test Plan will be allowed for a compound. Alternative tests may still be implemented by using a variation on the compound name. e.g. PVC-A, PVC-B, etc.
List of Key Sensors:
Bottle present at #1 Temp.
1 Temp. Queues full.
Bottle present in MPE #1 Std. #1.
Bottle present in MPE #1 Std. #2.
Bottle present at Infeed Chute.
Bottle present at Priority Chute.
Bottle present at #2 Temp. Queues.
2 Temp. Queues full.
Bottle present in MPE #2 Std. #1.
Bottle present in MPE #2 Std. #2.
Capping Station—1 sensor to indicate motion or jaws and/or rotation of jaws.
Air pressure sensor #1.

Bottle present at #3 Temp. Queues.
3 Temp. Queues full.
Bottle present in MPE #3 Std. #1.
Bottle present in MPE #3 Std. #2.
Die in Die Storage.
Die on Die loader/unloader.
Bottle present at #4 Temp. Queues.
4 Temp. Queues full.
Bottle present in MPE #4 Std. #1.
Bottle present in MPE #4 Std. #2.
Bottle in Priority Queue.
The following inputs exist on each MPE:
Tool Latch Open.
Die door closed.
Patches present at Patch dispenser.
Patch captured by robot.
Weights full up.
Motor unloaded.
'2' button on key pad activated.
Temp. in range.
Cell Configuration The cell 10 must be configured before it can be used. Configuration includes setting:

The temperatures at which the MPEs will operate.
How often the operator should be required to transfer files from the cell control computer to floppy diskettes.
Whether printer logging be allowed if a Material Test Plan requests it.
When standardization tests should be run on MPEs, and which Standard Material should be used.

Each MPE is provided with two bottles containing standardization material. The bottles are the standard size used for sample collection, but are marked with a unique bar code and color coded so that the operator is more sure to refill and replace the bottles correctly in the cell 10. Two bottles are provided to allow for the use of both a high and a low melt index standard on each MPE, but the operator may choose to fill them with the same Standard Material and test more frequently than would be possible if less Standard Material was available at the MPE. It is the operator's responsibility to fill the bottles with a Standard Material appropriate for the temperature being run in the associated MPE, and to correctly specify that material in the Cell Configuration mode.

Each Standard Material has an associated Material Test Plan, as do the sample materials. All Material Test Plans have a check-off box which permits the material under test to be declared a Standard Material, and to declare which Standard Material bottle it should be taken from.

Ideally, reconfiguration is performed infrequently. This expectation is on various aspects of cell operation. Each time the MPE operating temperatures are changed, all samples currently in the cell must be allowed to finish processing, then new Standard Material must be provided in the containers at each MPE.

Normal Operations

Figure 25:
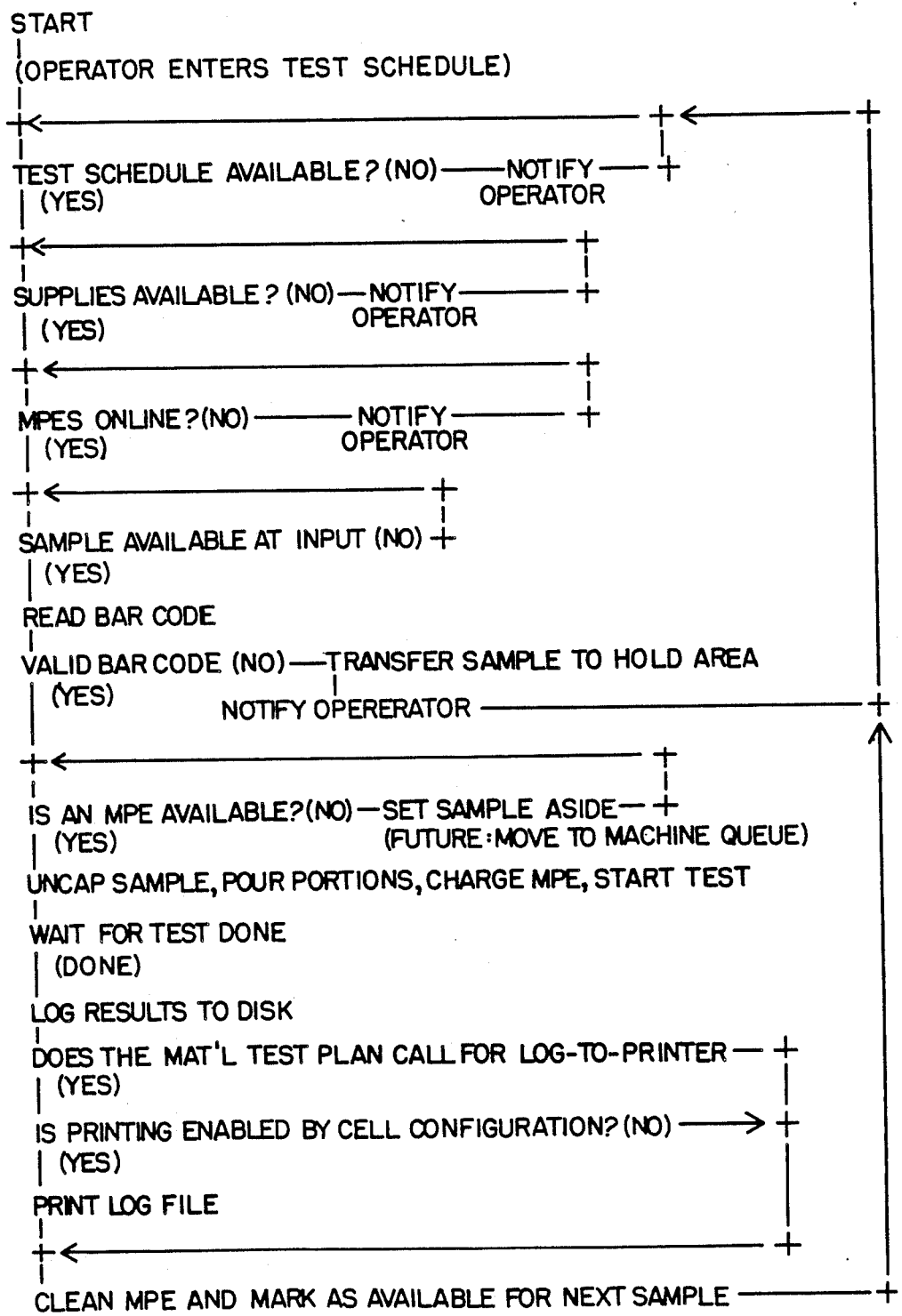
FIG. 25 is a flow chart of normal system operation.

FIG. 25 comprises a flow chart which graphically depicts the normal operation of the system.

Startup—The Test Schedule

At the beginning of a test period the operator inputs a Test Schedule to the system. The Test Schedule will indicate:

—Name of material to be tested (Material Type)
+ Location sample is to be collected from
+ Lot number (up to ten characters or digits)
+ Comment applicable to all samples in the group
—Date and times for sample collection (24:00 hr format, up to 24 times, max.) Collections spanning multiple dates will require multiple Test Schedule entries, one per date.

The items which are prefixed with a "+" are free-form comment fields in which anything of appropriate length can be entered. No checking for content or validity of these items is performed, but they are logged with the test results.

The data above will be used to generate a series of labels for the operator to affix to the bottles. Each label will have a unique six digit serial number represented in a bar code and will contain, in human readable format, the serial number, the material type (8 characters), the lot number (10 digits), and the date and time that the sample should be taken by the operator.

At the time the serial number is issued, it will be linked to a Material Test Plan (from the previously created library of Material Test Plans). When that serial number is later read by the bar code reader, the Material Test Plan instructions will be executed on the compound in the sample bottle.

Testing Samples

Samples in the previously mentioned bar coded containers are delivered to the input staging area of the test system. From there they are processed automatically. No operator input is needed at this time.

When a sample is processed by the system, the time and date at which the sample was to have been collected and the time and date at which it was processed by the system are all entered into the log. The presence of both times in the log allows administrative supervision of the system throughput lag as well as some supervision of thee operator's punctuality in sample collection.

Assuming that an MPE machine 13, 14 or 15 is available (clean and at the correct temperature) when a sample arrives at the input staging area, the robot 12 will pick it up, read the bar code at bar code reader 32, remove the bottle cap at capper 31, weigh out the required number of individual portions that make up the charge at balance 30, transfer the individual portions to the melt chamber 41 with the appropriate waits and ram cycles interposed, wait the specified time for the sample to reach the correct temperature, then lower the specified weights 43 and proceed with the test. At the end of the test, the MPE will send its report to the cell control computer to be recorded.

Each sample tested will generate a log entry consisting of the following information:

1—Material name;
2—Time and date the material was to have been collected;
3—Time and date the material was test was completed;
4—Serial number of the sample;
5—An optional comment entered by the operator. This comment will apply to the entire group of samples of this material type, and will appear on all the labels of the group. The comment will have been entered by the operator as part of the Test Schedule;
6—Raw test data as received from the MPE;
7—A second optional comment entered by the operator. This comment will NOT appear on the label, but only on the report; It may be entered anytime BEFORE the material sample is entered into the test cell. This comment area may be used by the operator to note that an individual sample was collected at a time significantly different from the specified time, for example; and 8—The MPE number on which the sample was run.

The test results of each sample will be recorded on the hard disk in the computer. Upon operator request, a number of log entries may be transferred to diskette for archival storage.

At the operator's option, the computer may print the test results of each sample as soon as testing is complete. This is in addition to the logging in the computer, which always takes place.

MPEs may operate at different temperatures. When the operator sets up the system, he specifies the operating temperature of the each of the MPEs. A sample queue 19 is maintained for each TEMPERATURE (not each) MPE), and will contain samples scheduled to run at that temperature. Since most samples are tested at either 190 degrees C. or 230 degrees C., it is probable that two or more MPEs 13, 14 or 15 will be operating at the same temperature. If this is the case, the physical queues 19 will be managed by the cell controller to merge two or more of them into a larger logical queue serving the multiple MPEs running at the same temperature. If one of the temperature queues 19 becomes full, no further samples will be taken from the sample infeed queue 16 until some space is again available in each temperature queue 19. To do so might cause the robot 12 to be "stuck" with a sample in its hand, and no place to put it.

If a material is input to the cell 10, but there is no MPE set to the appropriate temperature to test that material, the material will be placed in the output bin for operator attention.

Testing Priority Samples

In order to facilitate the expeditious handling of samples for which immediate test results are required, a priority to the cell 10 will be provided. Samples placed at the priority infeed queue 16 will bypass the waiting line in the regular infeed queue, and will be run on the next available MPE which is set at the correct temperature.

In order to accomplish this, an additional priority queue 21 will be associated with each temperature. This additional queue will have a depth of one bottle, and will be called the "priority queue" for that temperature. These priority queues 21 will be managed by the cell 10 control computer to merge one or more physical queues into a single logical queue when there are more physical queues than there are different MPE temperatures in the system.

Note that the same queue-filled situation exists with the priority queue as it does as noted above but that the priority queue system is separate from the regular queue system. If the priority queue system fills up, it will not directly affect induction of bottles into the station via the regular input queue. The converse is also true. The priority queue may have a depth of only one bottle, however, meaning that receipt of a single priority sample could temporarily preclude the induction of an additional priority sample, even though that sample is to be run at a different temperature.

Testing Standards

At intervals specified by the operator in the Cell Configuration mode, the system will run a Standard Material from standard queue 20 through a specified MPE and verify that the result is within an acceptable range. If the result is out of the acceptable range, the cell controller will remove that MPE 13, 14 or 15 from service and declare a Class 2 Exception Condition, summoning the operator.

Adding a Comment to a Single Sample

While the cell 10 is operating, the operator may "distract" the cell control computer long enough to add a comment to the log of an individual sample. This comment will appear only in the log, and may be used to record the fact that a sample was taken late, etc. This comment may be entered anytime prior to placing the sample into the cell.

Preparing and Using Diskettes

Before diskettes can be used to save log entries, they must be "Formatted" to prepare them for recording data. Formatting is a time intensive task, and may be done either on the cell control computer or on some other "AT" class computer. It may not be done on the cell control computer while the cell is in operation.

The operator may "distract" the cell control computer for the few seconds that it takes to show the directory of a diskette, and it may be possible to display the contents of specific files on the diskette. Implementation of this latter feature will depend on system timing and on client needs.

The operator may also "distract" the computer long enough to delete all the files from a diskette, allowing it to be reused.

Copying files from the hard disk to diskettes for archival storage is a task that will occupy the computer's full attention for the duration of the task, so it must be done during a time that the cell is not operating.

Daily Maintenance

When the operator selects "Daily Maintenance" from the Master Menu, all MPEs 13, 14 and 15 will finish the testing cycle they are in and they will be cleaned by the robot 12. The operator will be shown a maintenance checklist and asked to acknowledge that all items have been completed. Since the cell 10 will be in an idle condition at this time, the operator will be given the opportunity to format diskettes and to transfer files from the hard disk to a diskette. If log files on the hard disk have accumulated to the point where they would fill more than 75% of a diskette, the operator will be REQUIRED to copy them to a diskette before he will be allowed to proceed.

Exception Handling

Exceptions to routine operation will occur in all system. After designing the system to minimize the exceptions, the exceptions themselves must be dealt with.

The philosophy is to minimize the effect of an exception on the overall system. Where it is possible, practical, and safe to do so, the system should attempt to remain operational, even if at a reduced level.

Exceptions fall into two broad classes; those that require immediate operator intervention (class 1), and those that require eventual operator intervention (class 2).

Upon occurrence of a class 1 exception, the system should signal for operator intervention and tell the operator what caused the exception. In the case of a class 2 exception, the system should record the occurrence of the exception condition and work around it. If it is practical and safe to do so, the system should assist the operator in clearing exception conditions of both classes.

Summary of Exception Handling Details

Bottle Infeed System (16)

PROBLEM: Bottle present at end of infeed chute, but can't pick up. Bottle jammed at end of chute. Robot fingers can't pick-up bottle.
SOLUTION: Class 1. Alert Operator.
Bar Code Reader (32)
PROBLEM: Scanner not responding with any data after photocell broken indicating bottle present/or closing of jaws on capping station.
SOLUTION: Class 1. Alert Operator (Replacement of scanner may be necessary).
PROBLEM: Not a valid code read. Bar code defective or lost.
SOLUTION: Class 2. Alert operator. Put bottle in problem chute. If this problem occurs twice in a row, the scanner may not be working, declare a Class 1 exception and alert the operator.
PROBLEM: Multiple codes were read from a single bottle. Code defective or two codes on bottle.
SOLUTION: Class 2. Move to problem chute.
Bottle Capper (31)
PROBLEM: No bottle cap present or no bottle present (Robot dropped bottle from pick-up point).
SOLUTION: Class 1. Alert operator.
PROBLEM: Can't remove cap/motor overloading to attempt to remove.
SOLUTION: Class 2. Remove bottle to problem tray.
PROBLEM: Capping station won't rotate at all or doesn't respond to input signal from controller. Capping Station drive or controller defective.
SOLUTION: Class 1. Alert operator.
PROBLEM: Can't get bottle cap back on. Cap fell out of remover while bottle pouring at scale or cap tipped in clamp while removing.
SOLUTION: Class 2. Remove bottle to problem tray and cycle grippers on capping station.
Bottle In-system Queue
PROBLEM: Robot can't find bottle it put into queue.
SOLUTION: Class 1. Alert operator. (serious faults may be occurring)
Weigh Scale
PROBLEM: Balance not responding to commands (RS-232 communications).
SOLUTION: Class 1. Alert operator.
PROBLEM: Spilled material on balance
SOLUTION: Tare weight is off. Have robot pick-up and tip over the catch pan to remove spilled material.
Die Loading, Removal and Retrieval System
PROBLEM: Sensor doesn't find die on carrier after die removal. Die is lost and may not have been removed from chamber.
SOLUTION: Class 2. Remove the associated MPE from service and alert the operator.
PROBLEM: Pick-up system does not return to home after die pick-up.
SOLUTION: Class 2. Remove the associated MPE from service and alert the operator.
PROBLEM: Pick-up cylinder does not extend fully or retract fully.
SOLUTION: Class 2. Remove the associated MPE from service and alert the operator.
Die Magazine (33)
PROBLEM: Die 90 not released onto die loading pin. Problem with stacking system or solenoid is not releasing. SOLUTION: Class 2. Remove the associated MPE from service and alert the operator.
PROBLEM: Die supply exhausted.
SOLUTION: Class 2. Remove the associated MPE from service and alert the operator.
Cloth patch Dispenser (48)
PROBLEM: Cloth patch supply exhausted.
SOLUTION: Class 2. Remove the associated MPE from service and alert the operator.

Simplified Narrative of System Operation

The following is a description of the handling by cell 10 of one sample as it progresses through all the stations of the cell 10. It is assumed that the cell 10 has been configured, a Material Test Plan exists for the sample, and a Test Schedule has been set up anticipating the arrival of the material at the input of the cell.

The sample being processed through the cell will be processed along with many other samples which will be occupying the cell at the same time. In order to differentiate the sample from all the others, it is referred to as "S1."

SAMPLE COLLECTION:

At the time the Test Schedule was entered, a series of labels were printed for the bottle. Each label contained a unique bar code, instructions for the time and place of sample collection, and other information. One of the labels printed at that time was for S1, and was affixed to a bottle.

At the time designated for the collection of sample S1, a worker fills the S1 bottle with the material to be tested, caps it, and places the bottle in the "Infeed Queue" of the cell.

SAMPLE INPUT TO THE CELL:

After filling the S1 sample bottle, the operator places it in the Infeed Queue, where it is Queued behind sample bottles previously fed into the cell and not yet processed. Eventually the S1 sample reaches the head of the queue and is available for the robot to grasp.

SAMPLE IDENTIFICATION:

When (1) a sample is available at the head of the Infeed Queue and (2) the Robot Computer is ready to work with it, the robot will remove it from the Infeed Queue and place it in the capping station. The capper grasps the bottle cap and gently tries to tighten it while the robot holds the bottle. If the capper has a good grip on the bottle, no rotation of the capper jaws will be observed by the computer which will then command the robot to open its grip and allow the bottle to be rotated by the capper. During this rotation a bar code reader is able to read the bar code on the bottle label and identify the sample.

If the bar code cannot be identified as belonging in the current Test Schedule, the robot will drop it down the Problem Output Chute and declare a Class 2 Exception, calling for operator attention.

TEST PLAN SELECTION:

When a valid bar code is read, the Main Computer is able to associate (via the Test Schedule) that sample with a specific Material Test Plan.

QUEUING IN THE TEMPERATURE QUEUES:

One of the items on every Material Test Plan is the temperature at which the associated material must be tested. Each MPE runs at a constant temperature, established at the time the cell is configured. Queues are provided to Queue the samples that must wait for an available MPE of the correct temperature.

It is assumed that the S1 sample must wait for an MPE of the correct temperature to become available. S1 is therefore placed into one of the Temperature Queues.

MPE CHARGING:

Eventually, the S1 sample moves to the head of its Temperature Queue and an MPE of the correct temperature becomes available. At that time, the S1 bottle is removed from the Temperature Queue and returned again to the capping station where the bar code is verified. If all conditions are satisfied, the S1 bottle is uncapped and set on the electronic balance scale where the bottle and contents are weighed. (If the bottle appeared in the wrong queue or the cap cannot be removed, the bottle will be placed in the Problem Output Chute and a Class 2 Exception declared.)

The robot grasps the Vacuum Sipper and uses it to extract a portion of material from the S1 sample bottle. The size of a portion is determined by the total charge weight divided by the number of portions, both specified in the Material Test Plan. The portion is then deposited in the melt chamber of the MPE and the Tamping Tool is lowered to strip the sides of the melt chamber and to compact the melting mass at the bottom of the chamber. This sipping and tamping continues until all portions have been delivered to the MPE and the melt chamber holds the correct total sample weight.

To finish the charging step, the sample bottle is then capped and dropped down the Sample Output Chute. The Tamping Tool is removed from the MPE and cleaned. The test piston is installed in the MPE, the MPE test weight is selected, the change is effected by the robot, and the piston is lowered until it rests on the sample material in the test chamber. Finally, the Robot Computer reports to the Main Computer that the MPE has been charged.

BEGINNING THE TEST RUN:

Almost immediately upon receipt of the signal that the MPE has been charged, the Main Computer issues the command to the Robot Computer to simulate the pressing of the "Start" or "2nd" and "Start" keys on the MPE, beginning the automatic portion of the MPE test cycle.

MPE AUTOMATIC CYCLE:

This is part of the standard programming residing in the MPE. The sample material will be held in the melt chamber to liquify for a time which was originally entered in the Material Test Plan, and which was downloaded from there to the MPE by the Main Computer. Following the melting period, the test weight will be allowed to rest on the test piston, extruding the sample material through a calibrated orifice in a Removable Die.

The first Extrudate passing through the orifice tends to curl to one side or another and attach itself to anything it can reach, causing the flow of the Extrudate to be difficult to direct. This problem is eliminated by placing a silicone coated metal guard below the die orifice. Since the extrudate cannot adhere to this material, it falls straight to the Waste Chute and slides into the Waste Bin below. The Waste Chutes are silicone coated as well.

ENDING THE TEST RUN:

When the required amount of material has been extruded, the test is finished and the MPE transmits the resultant report to the Main Computer which captures and stores it. The test piston will continue to the bottom of the melt chamber to force out all remaining sample material, then it will remain there (to keep it hot) until it is removed for cleaning.

CLEANUP:

Upon receiving the command to clean a certain MPE from the Main Computer, the robot does the following sub-tasks:

Remove the test piston from the MPE, and wire brush it.

Insert the Chamber Pressurization Tool into the MPE and lower it with the maximum weight to pressurize the melt chamber with air, forcing out the sample Extrudate which remains in the Removable Die orifice.

Remove the Removable Die from the melt chamber, using the Die Tool in combination with the Chamber Pressurization Tool. Place the die in the ultrasonic tank for cleaning.

Clean the melt chamber, using Cleaning Patches and the Chamber Cleaning Tool. As the robot attempts the removal of each patch from the Patch Dispenser, a photocell detects that the robot grippers have succeeded in grasping and pulling a patch. As the robot hand moves away, the same photocell checks to be sure a second patch did not pull partially out as the first one was removed. The patch is placed across the mouth of the melt chamber, then the Chamber Cleaning Tool forces the patch down through the chamber on the tip of a rotating rod. The rod is long enough that both it and the patch exit the melt chamber at the bottom, where the patch is stripped from the rod tip as the rod is withdrawn. The patch falls to the Waste Chute and into the Waste Bin.

Replace the Chamber Pressurization Tool into its storage rack. Get the Tamping Tool from a tool holder and insert it into the MPE.

Using the Die Tool, remove a die from the Die Magazine and install it at the bottom of the melt chamber.

Notify the Main Computer that the MPE is cleaned and available for the next sample.

EXCEPTION DETECTION AND PROCESSING:

Whenever practical, cell operations and supply levels are checked by independent sensors. In general, as supplies levels become low the operator will be summoned. If a cell operation fails it will be attempted one more time. If it fails a second time, the operator will be summoned.

We claim:

1. In a melt indexer for determining the melt index of a plastic by testing, said melt indexer having a melt chamber in which a sample of plastic to be tested is placed, heating means for melting the sample to a predetermined temperature and a test piston for extruding the melted sample through a calibrated orifice of a removable die to determine the viscosity of the sample as a function of its temperature, the combination therewith of an automated test system which comprises:

(a) a robot and a computer programmable to control the movement of the robot;

(b) an infeed queue for holding a plurality of containers containing samples to be tested;

(c) identification means for identifying each sample to the tested;

(d) a test computer for associating a particular sample with a predetermined plan for testing the sample, recording and processing the melt index test results;

(e) extracting means for extracting a charge of the sample from the sample container and placing it in the melt chamber;

(f) cleaning means for cleaning the test piston and melt chamber after the test is complete and preparing the apparatus for the next test;
(g) means for detecting and processing exceptions to proper operation of the apparatus;
(g) said robot being operable to:
(i) select a container from the infeed queue;
(ii) hold the container while the sample container is identified;
(iii) open the container;
(iv) hold the container while operating said extracting means to extract a charge from the sample container and place it in the melt chamber; and
(v) manipulate said cleaning means.

2. In a melt indexer for determining the melt index of a plastic according to claim 1, and including a plurality of melt indexers positioned in relation to each other and to one said robot arm for being serviced, in turn, by said one robot.

3. In a melt indexer for determining the melt index of a plastic according to claim 2, and including a plurality of temperature queues for holding a plurality of samples in a given order to be tested by a certain one of said plurality of melt indexers operating at the proper temperature for the sample.

4. In a melt indexer for determining the melt index of a plastic according to claim 1 or 2 wherein said identification means comprises a bar code reader for reading bar codes on the containers.

5. In a melt indexer for determining the melt index of a plastic according to claim 4, wherein said extracting means comprises a vacuum operated sipper for extracting a precise quantity of sample from the container and placing it in the melt chamber.

6. In a melt indexer for determining the melt index of a plastic according to claim 5, wherein said vacuum operated sipper extracts the sample to be tested from the container and places the sample in the melt chamber in increments, and wherein said melt indexer includes a tamping tool to move down the melt chamber between additions of the sample to the melt chamber to strip any sample on the sides of the melt chamber and compact the mass of melting sample at the bottom of the melt chamber.

7. In a melt indexer for determining the melt index of a plastic according to claim 6, wherein said robot includes means for installing and removing said tamping tool and said test piston from the melt indexer.

8. In a melt indexer for determining the melt index of a plastic according to claim 1 or 2, wherein said cleaning means comprises means for brushing and ultrasonically treating the removed test piston, pressurizing means for pressurizing the test chamber with high pressure air to force out any sample remaining in the melt chamber after the melt indexing test is completed, means for removing the removable die from the bottom of the melt chamber for cleaning, and means for cleaning the melt chamber.

9. In a melt indexer for determining the melt index of a plastic according to claim 8, wherein said cleaning means for cleaning the melt chamber includes means for inserting a cloth cleaning patch over the melt chamber and forcing the patch down through the melt chamber to the bottom.

10. In a melt indexer for determining the melt index of a plastic according to claim 9, and including means for rotating the cloth patch as it is moved down the length of the melt chamber.

11. In a melt indexer for determining the melt index of a plastic according to claim 8, wherein said cleaning means includes an ultrasonic bath for cleaning said removable die.

12. In a melt indexer for determining the melt index of a plastic according to claim 1 or 2, and including means for storing a plurality of removable dies for loading into the melt indexer by said robot.

13. In a melt indexer for determining the melt index of a plastic according to claim 1 or 2, wherein said container comprises a bottle with a screw cap, and wherein said robot includes means for applying and removing caps from the bottle.

14. In a melt indexer for determining the melt index of a plastic according to claim 13, wherein said robot applies a predetermined low tightening torque for applying the cap to the bottle and a predetermined high torque for removing the cap from the bottle.

15. A melt indexer system for determining the melt index of a plastic by testing said melt indexer system comprising:
(a) a plurality of melt indexers, each of said melt indexers including a melt chamber in which a sample of plastic to be tested is placed, heating means for melting the sample to a predetermined temperature and a test piston for extruding the melted sample through a calibrated orifice of a removable die to determine the viscosity of the sample as a function of its temperature;
(b) a robot arm and a computer programmable to control the movement of the robot arm;
(c) an infeed queue for holding in predetermined order a plurality of containers containing samples to be tested;
(d) identification means for identifying each sample to the tested;
(e) a test computer for associating a particular sample with a predetermined plan for testing the sample, recording and processing the melt index test results;
(f) extracting means for extracting a charge of the sample from the sample container and placing it in the melt chamber;
(g) cleaning means for cleaning the test piston and melt chamber after the test is complete and preparing the apparatus for the next test;
(h) means for detecting and processing exceptions to proper operation of the apparatus;
(i) said robot arm being operable to:
(i) select a container from the infeed queue;
(ii) hold the container while the sample container is identified;
(iii) open the container;
(iv) hold the container while operating said extracting means to extract a charge from the sample container and place it in the melt chamber; and
(v) manipulate said cleaning means.

16. A melt indexer system for determining the melt index of a plastic according to claim 15, and including a plurality of melt indexers positioned in relation to each other and to one said robot arm for being serviced, in turn, by said one robot arm.

17. A melt indexer system for determining the melt index of a plastic according to claim 16, and including a plurality of temperature queues for holding a plurality of samples in a given order to be tested by a certain one of said plurality of melt indexers operating at the proper temperature for the sample.

18. A melt indexer system for determining the melt index of a plastic according to claim 15 or 16 wherein said identification means comprises a bar code reader for reading bar codes on the containers.

19. A melt indexer system for determining the melt index of a plastic according to claim 18, wherein said extracting means comprises a vacuum operated sipper for extracting a precise quantity of sample from the container and placing it in the melt chamber.

20. A melt indexer system for determining the melt index of a plastic according to claim 19, wherein said vacuum operated sipper extracts the sample to be tested from the container and places the sample in the melt chamber in increments, and wherein said melt indexer includes a tamping tool to move down the melt chamber between additions of the sample to the melt chamber to strip any sample on the sides of the melt chamber and compact the mass of melting sample at the bottom of the melt chamber.

21. A melt indexer system for determining the melt index of a plastic according to claim 20, wherein said robot arm includes means for installing and removing said tamping tool and said test piston from the melt indexer.

22. A melt indexer system for determining the melt index of a plastic according to claim 15 or 16, wherein said cleaning means comprises means for brushing and ultrasonically treating the removed test piston, pressurizing means for pressurizing the test chamber with high pressure air to force out any sample remaining in the melt chamber after the melt indexing test is completed, means for removing the removable die from the bottom of the melt chamber for cleaning, and means for cleaning the melt chamber.

23. A melt indexer system for determining the melt index of a plastic according to claim 22, wherein said cleaning means for cleaning the melt chamber includes means for inserting a cloth cleaning patch over the melt chamber and forcing the patch down through the melt chamber to the bottom.

24. A melt indexer system for determining the melt index of a plastic according to claim 23, and including means for rotating the cloth patch as it is moved down the length of the melt chamber.

25. A melt indexer system for determining the melt index of a plastic according to claim 22, wherein said cleaning means includes an ultrasonic bath for cleaning said removable die.

26. A melt indexer system for determining the melt index of a plastic according to claim 15 or 16, and including means for storing a plurality of removable dies in sequential order for loading into the melt indexer by said robot arm.

27. A melt indexer system for determining the melt index of a plastic according to claim 15 or 16, wherein said container comprises a bottle with a screw cap, and wherein said robot arm includes means for applying and removing caps from the bottle.

28. A melt indexer system for determining the melt index of a plastic according to claim 27, wherein said robot applies a predetermined low tightening torque for applying the cap to the bottle and a predetermined high torque for removing the cap from the bottle.

* * * * *